(12) United States Patent
Ho et al.

(10) Patent No.: US 6,482,976 B1
(45) Date of Patent: Nov. 19, 2002

(54) PROCESSES FOR CONDUCTING EQUILIBRIUM-LIMITED REACTIONS

(75) Inventors: Fungau Ho, Charleston, WV (US); Leah Ann Patterson, South Charleston, WV (US); Cyril B. Tellis, Charleston, WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/361,395

(22) Filed: Jul. 26, 1999

Related U.S. Application Data

(63) Continuation-in-part of application No. 09/335,341, filed on Jun. 17, 1999.

(51) Int. Cl.[7] ......................... C07C 69/52; C07C 67/02
(52) U.S. Cl. ..................................... 560/205; 560/265
(58) Field of Search ................................ 560/205, 265

(56) References Cited

U.S. PATENT DOCUMENTS

| | | | | |
|---|---|---|---|---|
| 2,645,660 A | * | 7/1953 | Drout et al. | |
| 3,700,726 A | | 10/1972 | Johnson et al. | 260/491 |
| 4,280,010 A | * | 7/1981 | Erpenbach et al. | |
| 4,748,268 A | * | 5/1988 | Pietsch et al. | |
| 5,734,074 A | | 3/1998 | Dockner et al. | 560/205 |
| 5,900,125 A | | 5/1999 | Exner et al. | 203/60 |

FOREIGN PATENT DOCUMENTS

| | | |
|---|---|---|
| EP | 733617 A1 | 9/1996 |
| EP | 779268 A1 | 6/1997 |
| EP | 0916643 A1 | 5/1999 |
| WO | 9852903 | 11/1998 |
| WO | 9852904 | 11/1998 |

* cited by examiner

*Primary Examiner*—Alan L. Rotman
*Assistant Examiner*—Taylor V. Oh

(57) ABSTRACT

This invention relates to processes for conducting equilibrium-limited reactions such as esterification and alcoholysis reactions, using a single reaction zone and an acid separation column containing a rectification zone and a stripping zone. The single reaction zone temperature and pressure are sufficient to crack heavies, e.g., Michael-Addition heavies, formed in or introduced into said single reaction zone and to vaporize at least a portion of the product upon production thereof. The rate of supply of withdrawn bottoms fraction from the acid separation column to the single reaction zone can be controlled and adjusted to provide stable and efficient operation of the acid separation column and single reaction zone.

25 Claims, 1 Drawing Sheet

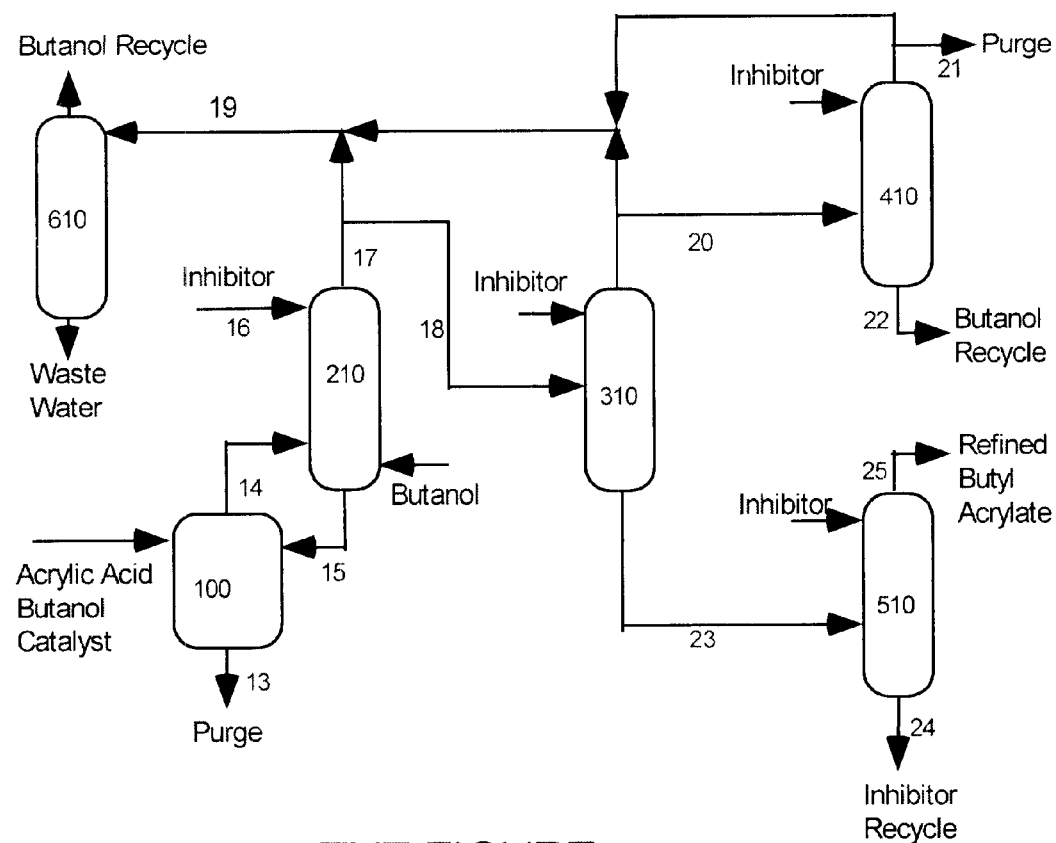
THE FIGURE

PROCESSES FOR CONDUCTING EQUILIBRIUM-LIMITED REACTIONS

This application is a continuation-in-part of U.S. patent application Ser. No. 09/335,341, filed Jun. 17, 1999.

BRIEF SUMMARY OF THE INVENTION

1. Technical Field

This invention pertains to processes for producing reaction product through equilibrium-limited reactions, such as esterification and alcoholysis (or transesterification) reactions. The invention is particularly useful in esterification processes such as to make carboxylic acid esters, e.g., butyl acrylate and ethylhexyl acrylate.

2. Background of the Invention

Equilibrium-limited reactions generally involve the reaction of two or more reactants to produce at least one product and, typically, a co-product. In order to achieve a greater conversion to the desired product(s), various techniques have been suggested such as removing the co-product and/or product from the reaction menstruum to maintain a driving force toward the product.

Equilibrium-limited reactions can be conducted in a single reactor with product being selectively removed from the reaction menstruum or in a plurality of reactors in which product is separated from the reaction menstruum in each of the reactor stages. One type of single reactor process is disclosed in U.S. Pat. No. 3,700,726 which discloses a process for making glycol ether acetates in which a reactor operates at a temperature of about 150° C. to 225° C. and a pressure of about 25 psia to about 150 psia to effect the reaction of a lower alkyl acetate with a glycol ether in the presence of catalyst selected from aluminum alkoxides, titanium alkoxides and dialkyl tin oxides. A vapor is withdrawn from the reactor and is distilled to recover the co-product alcohol and a bottoms fraction which is recycled to the reactor. A liquid is withdrawn from the reactor and is flashed in a flash column operating at about 130° C. to 180° C. The overhead from the flash column contains the product ester which is subjected to distillation for purification and the bottoms from the flash column, which contains catalyst, is recycled to the reactor.

Another type of single reactor process is disclosed in U.S. Pat. No. 4,280,010 which discloses a continuous process for making alkyl acrylates free from ether by reacting acrylic acid with a C1 to C4 alkanol in a molar ratio of 1:1 to 1:2 in the liquid phase. The process is conducted at a temperature of 80° C. to 130° C. and a pressure of 100 to 760 mm Hg in the presence of a sulfuric acid or organic sulfonic acid catalyst, and the resulting alkyl acrylate is distillatively purified. As part of the distillation, an azeotropic mixture of alkyl acrylate, reaction water and unreacted alkanol is distilled off near the head of a first distillation zone which is mounted on the reaction zone.

Yet another type of single reactor process is disclosed in European Patent No. 0 733 617 which discloses a process for the continuous esterification of an alkanol with (meth) acrylic acid in the presence of proton-donating catalysts in a homogeneous, liquid, solvent-free phase in which the water generated in the reaction and the produced alkyl esters are continuously separated as an aqueous azeotrope via the head of a rectification zone mounted on the reaction zone and which has a head pressure of 0.1–1 atmospheres, to give a pure (meth)acrylate.

European Patent Application No. 0 779 268 discloses a method for recovering n-butyl acrylate substantially free of acrylic acid from an esterification reaction mixture by distilling from an esterification reactor a vaporized mixture of acrylic acid, n-butyl acrylate, n-butanol and water, and condensing the vaporized mixture to provide a first condensate of an organic phase and an aqueous phase. A portion of the organic phase and aqueous phase is then fed to an acrylic acid separation column. An azeotropic mixture of n-butanol, n-butyl acrylate and water is distilled from the acrylic acid separation column at an aqueous reflux ratio of 8.5:1 to 17:1, and an acrylic acid bottom stream is removed from the distillation column and recycled to the esterification reactor. Refluxing any portion of the organic phase is detrimental to the operation of the acrylic acid separation column (see page 13, line 58 through page 14, line 5). The overhead mixture is condensed to provide a second condensate which is separated into a n-butyl acrylate rich organic phase and an aqueous phase. The n-butyl acrylate rich organic phase is then removed substantially free of acrylic acid. Additional reactants are recovered and recycled after treatment in a separate hydrolytic recovery unit and a cracking reactor.

Frequently, where the reaction is conducted in a single reactor, the residence time to secure the desired conversion results in a large reactor volume per unit volume of product. Moreover, substantial amounts of vapor are typically generated to remove product and co-product, and vaporized reactants are recovered and returned to the reactor, resulting in significant energy costs. Reactant recovery itself may pose difficult problems or require elaborate separation schemes. In some instances, to vaporize the product for its removal, temperatures may be required that result in undesired side reactions and/or subatmospheric pressures are employed that further increase operating costs.

Accordingly, processes for conducting equilibrium-limited reactions are sought that reduce total reactor volumes and number of reactors, minimize reactant recovery problems, and provide sought conversions to the product without the need to resort to significant energy use, e.g., unduly high temperatures or excessive vacuums, in conducting the reactions.

DISCLOSURE OF THE INVENTION

The processes of this invention relate to conducting an equilibrium-limited reaction of at least one carboxylic acid and at least one alcohol to produce at least one ester product in a single reaction zone, wherein the reaction zone temperature and pressure are sufficient to crack heavies, e.g., Michael-Addition heavies, formed in or introduced into said single reaction zone and to vaporize at least a portion of the ester product upon production thereof. An acid separation column containing a rectification zone and a stripping zone provides (in the rectification zone) an overhead fraction comprising the at least one ester product and (in the stripping zone) a bottoms fraction comprising water and the at least one carboxylic acid, in which at least a portion of the bottoms fraction is supplied by controlled means to the single reaction zone sufficient to provide stable and efficient operation of the acid separation column and single reaction zone. While typically only one ester product is ultimately sought, the processes of this invention may make possible the simultaneous formation of two or more ester products. For instance, acrylic acid may be reacted with a mixture of ethanol and butanol to produce the corresponding ethyl and butyl acrylates.

The processes of this invention relate in part to conducting an equilibrium-limited reaction of at least one carboxylic acid and at least one alcohol to produce at least one ester product comprising:

a. reacting at least one carboxylic acid-containing feedstock with at least one alcohol-containing feedstock in the presence of an esterification catalyst in a single reaction zone maintained under reaction conditions sufficient to produce at least one ester product, said reaction conditions comprising a temperature and pressure sufficient to crack heavies formed in or introduced into said single reaction zone and to vaporize at least a portion of said at least one ester product upon production thereof;

b. withdrawing vapor from said single reaction zone, and introducing said withdrawn vapor into the lower portion of an acid separation column, said acid separation column comprising a rectification zone above the point where said withdrawn vapor is introduced into said acid separation column and a stripping zone below the point where said withdrawn vapor is introduced into said acid separation column, to provide (in said rectification zone) an overhead fraction comprising said at least one ester product and (in said stripping zone) a bottoms fraction comprising water and said at least one carboxylic acid;

c. withdrawing from the acid separation column the bottoms fraction and supplying at least a portion of the withdrawn bottoms fraction to said single reaction zone by controlled means sufficient to provide stable and efficient operation of said acid separation column and said single reaction zone; and d. withdrawing from the acid separation column the overhead fraction and recovering said at least one ester product from the overhead fraction.

In this embodiment, lower purity feed streams, for example, crude butanol streams containing dibutyl ether or crude acrylic acid streams containing high concentrations of acrylic acid dimer or other Michael-Addition heavies may be utilized in the processes of this invention as well as heavy residue-containing streams generated from other processes which employ similar equilibrium-limited reactions, e.g., integrated equilibrium-limited processes. Also, in this embodiment, the rate of supply of withdrawn bottoms fraction from the acid separation column to the single reaction zone can be controlled and adjusted according to the needed water rate for formation of the product/water azeotrope, e.g., butyl acrylate/water azeotrope. If the rate is too low, the liquid level in the single reaction zone will rise due to buildup of product, e.g., butyl acrylate, concentration leading to inefficient operation of the single reaction zone. If the rate is too high, the excess water will remove byproduct, e.g., butoxy propionate (BBP), from the single reaction zone by a BBP/water azeotrope, which results in a higher BBP concentration in the acid separation column leading to unstable and inefficient operation of the acid separation column.

The processes of this invention also relate in part to conducting an equilibrium-limited reaction of at least one carboxylic acid and at least one alcohol to produce at least one ester product comprising:

a. reacting at least one carboxylic acid-containing feedstock with at least one alcohol-containing feedstock in the presence of an esterification catalyst in a single reaction zone maintained under reaction conditions sufficient to produce at least one ester product, said reaction conditions comprising a temperature and pressure sufficient to crack heavies formed in or introduced into said single reaction zone and to vaporize at least a portion of said at least one ester product upon production thereof;

b. withdrawing vapor from said single reaction zone, and introducing said withdrawn vapor into the lower portion of an acid separation column, said acid separation column comprising a rectification zone above the point where said withdrawn vapor is introduced into said acid separation column and a stripping zone below the point where said withdrawn vapor is introduced into said acid separation column, to provide (in said rectification zone) an overhead fraction comprising said at least one ester product and (in said stripping zone) a bottoms fraction comprising water and said at least one carboxylic acid;

c. introducing at least one alcohol, which may be the same or different as the alcohol contained in said alcohol-containing feedstock, into said acid separation column in the region between the bottom of the acid separation column and the point where said withdrawn vapor is introduced into the acid separation column, in an amount sufficient to provide stable and efficient operation of said acid separation column, e.g., minimize or eliminate foaming in said acid separation column;

d. withdrawing from the acid separation column the bottoms fraction and supplying at least a portion of the withdrawn bottoms fraction to said single reaction zone by controlled means sufficient to provide stable and efficient operation of said acid separation column and said single reaction zone; and e. withdrawing from the acid separation column the overhead fraction and recovering said at least one ester product from the overhead fraction.

In this embodiment, operational stability is imparted to the acid separation column through introduction of the alcohol, either fresh or recycled, into the acid separation column in the region between the bottom of the acid separation column and the point where the withdrawn vapor from the single reaction zone is introduced into the acid separation column. It is important to control foaming in the distillation column base not only for operational stability and efficiency but also for minimizing carboxylic acid breakthrough in the overhead make. Foaming may result from unstable composition regions and/or a high base circulation rate in the acid separation column.

The processes of this invention further relate in part to conducting an equilibrium-limited reaction of at least one unsaturated carboxylic acid and at least one alcohol to produce at least one unsaturated ester product comprising:

a. reacting at least one unsaturated carboxylic acid-containing feedstock with at least one alcohol-containing feedstock in the presence of an esterification catalyst in a single reaction zone maintained under reaction conditions sufficient to produce at least one unsaturated ester product, said reaction conditions comprising a temperature and pressure sufficient to crack heavies formed in or introduced into said single reaction zone and to vaporize at least a portion of said at least one unsaturated ester product upon production thereof;

b. withdrawing vapor from said single reaction zone, and introducing said withdrawn vapor into the lower portion of an acid separation column, said acid separation column comprising a rectification zone above the point where said withdrawn vapor is introduced into said acid separation column and a stripping zone below the point where said withdrawn vapor is introduced into said acid separation column, to provide (in said rectification zone) an overhead fraction comprising said at least one unsaturated ester product, lower boiling byproducts, higher boiling byproducts and said at least one alcohol, and (in said stripping zone) a bottoms fraction comprising water and said at least one unsaturated carboxylic acid, and introducing at least one polymerization inhibitor into said acid separation column;

c. withdrawing from the acid separation column the bottoms fraction and supplying at least a portion of the withdrawn bottoms fraction to said single reaction zone by controlled means sufficient to provide stable and efficient operation of said acid separation column and said single reaction zone;

d. withdrawing from the acid separation column the overhead fraction and introducing at least a portion of the withdrawn overhead fraction into at least one splitter distillation column to provide an overhead fraction comprising said lower boiling byproducts and said at least one alcohol and a bottoms fraction comprising said at least one unsaturated ester product and said higher boiling byproducts, and introducing at least one polymerization inhibitor into said at least one splitter distillation column;

e. withdrawing from the at least one splitter distillation column the overhead fraction and introducing the withdrawn overhead fraction into at least one alcohol recovery distillation column to provide an overhead fraction comprising said lower boiling byproducts and a bottoms fraction comprising said at least one alcohol, and introducing at least one polymerization inhibitor into said at least one alcohol recovery distillation column;

f. withdrawing from the at least one alcohol recovery distillation column the bottoms fraction (and recycling at least a portion of said bottoms fraction) and the overhead fraction (and purging at least a portion of said overhead fraction);

g. withdrawing from the at least one splitter distillation column the bottoms fraction and introducing the withdrawn bottoms fraction into at least one ester distillation column to provide an overhead fraction comprising said at least one unsaturated ester product and a bottoms fraction comprising said higher boiling byproducts and at least one polymerization inhibitor, and introducing at least one polymerization inhibitor into said at least one ester distillation column and/or said withdrawn bottoms fraction from the at least one splitter distillation column prior to introducing said withdrawn bottoms fraction into said at least one ester distillation column;

h. withdrawing from the at least one ester distillation column the bottoms fraction comprising at least one polymerization inhibitor and supplying at least a portion of the withdrawn bottoms fraction to the acid separation column, the at least one splitter distillation column and/or the at least one alcohol recovery distillation column, in an amount sufficient to minimize or eliminate polymerization of said unsaturated carboxylic acid and/or said unsaturated ester product; and i. withdrawing from the at least one ester distillation column the overhead fraction comprising said at least one unsaturated ester product.

In this embodiment, polymerization inhibitors are reused in the process by recycling the withdrawn bottoms fraction containing polymerization inhibitor from the at least one ester distillation column to the acid separation column, the at least one splitter distillation column and/or the at least one alcohol recovery distillation column. In addition to being cost effective, the recycling of polymerization inhibitors to the various distillation columns controls undesirable polymerization, for example, reactive monomers such as acrylic acid and butyl acrylate readily form polymer via free radical polymerization if not well inhibited. This process is further cost effective in that the recycle stream returns heavies for cracking to the reactor.

The processes of this invention yet further relate in part to conducting an equilibrium-limited reaction of at least one carboxylic acid and at least one alcohol to produce at least one ester product comprising:

a. reacting at least one carboxylic acid-containing feedstock with at least one alcohol-containing feedstock in the presence of an esterification catalyst in a single reaction zone maintained under reaction conditions sufficient to produce at least one ester product, said reaction conditions comprising a temperature and pressure sufficient to crack heavies formed in or introduced into said single reaction zone and to vaporize at least a portion of said at least one ester product upon production thereof;

b. withdrawing vapor from said single reaction zone, and introducing said withdrawn vapor into the lower portion of an acid separation column, said acid separation column comprising a rectification zone above the point where said withdrawn vapor is introduced into said acid separation column and a stripping zone below the point where said withdrawn vapor is introduced into said acid separation column, to provide (in said rectification zone) an overhead fraction comprising said at least one ester product, lower boiling byproducts, higher boiling byproducts and said at least one alcohol, and (in said stripping zone) a bottoms fraction comprising water and said at least one carboxylic acid;

c. withdrawing from the acid separation column the bottoms fraction and supplying at least a portion of the withdrawn bottoms fraction to said single reaction zone by controlled means sufficient to provide stable and efficient operation of said acid separation column and said single reaction zone;

d. withdrawing from the acid separation column the overhead fraction and introducing at least a portion of the withdrawn overhead fraction into at least one splitter distillation column to provide an overhead fraction comprising said lower boiling byproducts and said at least one alcohol and a bottoms fraction comprising said at least one ester product and said higher boiling byproducts;

e. withdrawing from the at least one splitter distillation column the bottoms fraction and introducing the withdrawn bottoms fraction into at least one ester distillation column to provide an overhead fraction comprising said at least one ester product and a bottoms fraction comprising said higher boiling byproducts;

f. withdrawing from the at least one ester distillation column the bottoms fraction (and recycling at least a portion of said bottoms fraction) and the overhead fraction (comprising at least said one ester product);

g. withdrawing from the at least one splitter distillation column the overhead fraction and introducing the withdrawn overhead fraction into at least one alcohol recovery distillation column to provide an overhead fraction comprising said lower boiling byproducts and a bottoms fraction comprising said at least one alcohol;

h. withdrawing from the at least one alcohol recovery distillation column the bottoms fraction and supplying at least a portion of the withdrawn bottoms fraction to said acid separation column in the region between the bottom of the acid separation column and the point where said withdrawn vapor is introduced into the acid separation column, in an amount sufficient to provide stable and efficient operation of said acid separation column, e.g., minimize or eliminate foaming in said acid separation column, and/or said single reaction zone; and i. withdrawing from the at least one alcohol recovery distillation column the overhead fraction (and purging at least a portion of the withdrawn overhead fraction).

In this embodiment, unreacted alcohol is reused in the process by recycling the withdrawn bottoms fraction containing unreacted alcohol from the at least one alcohol recovery distillation column to the acid separation column in the region between the bottom of the acid separation column and the point where the withdrawn vapor from the single reaction zone is introduced into the acid separation column and/or said single reaction zone. In addition to being cost effective, the recycling of unreacted alcohol to the acid separation column helps to impart operational stability to the acid separation column as described above.

In another embodiment, the above processes also comprise introducing at least a portion of (i) the withdrawn overhead fraction from the acid separation column, (ii) the withdrawn overhead fraction from the at least one splitter distillation column, and/or (iii) the withdrawn overhead fraction from the at least one alcohol recovery distillation column, to a water distillation column to provide an overhead fraction comprising said at least one alcohol and a bottoms fraction comprising water, withdrawing from the water distillation column the bottoms fraction (and purging at least a portion of the bottoms fraction), and withdrawing from the water distillation column the overhead fraction and supplying at least a portion of the overhead fraction to said acid separation column in the region between the bottom of the acid separation column and the point where said withdrawn vapor from the single reaction zone is introduced into the acid separation column and/or said single reaction zone. In this embodiment, unreacted alcohol is reused in the process by recycling as described above.

In yet another embodiment, this invention relates to a batchwise or continuously generated mixture comprising at least 50.0 weight percent butyl acrylate and containing not more than 8 parts per million acrylic acid. Such mixtures result from the practice of this invention when carboxylic acid, e.g., acrylic acid, breakthrough in the overhead make from the acid separation column is minimized or eliminated. The unique configuration of the single reaction zone and acid separation column is advantageous in enabling the production of an overhead make (from the acid separation column) having high concentrations of butyl acrylate, e.g., at least 50.0 weight percent, and having low concentrations of acrylic acid, e.g., not more than 10 parts per million, preferably not more than 8 parts per million, and more preferably not more than 5 parts per million, as described herein. Higher concentrations of acrylic acid may be detrimental for obtaining desirable butyl acrylate quality. Having lower concentrations of acrylic acid in the butyl acrylate stream can eliminate the need for further processing, e.g., the need to reduce acrylic acid by neutralization.

The processes of this invention further relate in part to conducting an equilibrium-limited reaction of at least one carboxylic acid and at least one alcohol to produce at least one ester product comprising reacting at least one carboxylic acid-containing feedstock with at least one alcohol-containing feedstock in the presence of an esterification catalyst in a single reaction zone maintained under reaction conditions sufficient to produce at least one ester product, said reaction conditions comprising a temperature and pressure sufficient to crack heavies formed in or introduced into said single reaction zone and to vaporize at least a portion of said at least one ester product upon production thereof, and wherein said at least one carboxylic acid-containing feedstock comprises a crude acrylic acid stream containing acetic acid, acrylic acid dimer and/or other Michael-Addition heavies. In this embodiment, lower purity feed streams, for example, crude acrylic acid streams containing high concentrations, e.g., greater than about 0.25 weight percent or even greater than about 0.5 weight percent, of acrylic acid dimer and/or other Michael-Addition heavies may be utilized in the processes of this invention.

The processes of this invention find particular application in the production of esters, especially esters that contain ethylenic unsaturation or other reactive groups that can lead to unwanted side reactions. Advantageous processes include the formation of alkyl acrylates and alkyl methacrylates from lower alkanols, typically alcohols of one to twelve carbon atoms, and acrylic acid or methacrylic acid. A preferred aspect of this invention pertains to processes for making butyl acrylate from butanol and acrylic acid.

BRIEF DESCRIPTION OF THE DRAWING

The FIGURE is a simplified schematic depiction of a process for making butyl acrylate from acrylic acid and butanol in accordance with this invention.

DETAILED DESCRIPTION

This invention relates to processes for conducting equilibrium-limited reaction processes. This invention pertains broadly to any equilibrium-limited reaction process; however, the processes find most useful applications in producing organic equilibrium products, especially esters. The processes may be batch processes, but are preferably continuous processes in which the reactants and any adjuvants such as catalysts, inhibitors and solvents, are added periodically or uninterruptedly to, and products are removed periodically or uninterruptedly from, the reaction zone. The following discussion references the use of at least two reactants for the sake of convenience. It should be understood in the aspects of this invention where a single reactant is used for the equilibrium-limited reaction, that the description applies equally. Similarly, reference is made to a co-product for the sake of convenience. It should be recognized that equilibrium-limited reactions where no co-product is formed are encompassed by the invention.

Typical equilibrium-limited reaction processes include esterification and alcoholysis reactions. Esterification reactions involve the production of an ester by reaction of an alcohol with a carboxylic acid. A co-product, water, is also produced. In alcoholysis (transesterification) reactions, an ester is reacted with an alcohol with an interchange occurring.

The carboxylic acids used in the processes of this invention often can be represented by the formula R'C(O)OH, wherein R' is a hydrocarbyl-containing group of 1 to about 8, preferably 1 to about 4, carbon atoms and may be saturated or unsaturated aliphatic or cycloaliphatic (including branched and unbranched aliphatic and cycloaliphatic which may be saturated or contain ethylenic unsaturation), aryl, alkaryl (cyclic, linear and branched alkyl), aralkyl (cyclic, linear and branched alkyl), or any of the preceding containing a hetero atom such as oxygen, sulfur, nitrogen and phosphorus, and R' may be substituted with one or more hetero atom-containing substituents such as halides. In alcoholysis processes, the esters generally can be represented by the formula R'C(O)OR" wherein R' is as defined above and R" is a hydrocarbyl-containing group of 1 to about 12, preferably 1 to about 8, carbon atoms and may be saturated or unsaturated aliphatic or cycloaliphatic (including branched and unbranched aliphatic and cycloaliphatic which may be saturated or contain ethylenic unsaturation), aryl, alkaryl (cyclic, linear and branched alkyl), aralkyl (cyclic, linear and branched alkyl), or any of the preceding containing a heteroatom such as oxygen, sulfur, nitrogen or phosphorus. The alcohols can be represented by the formula R'''OH wherein R''' is a hydrocarbyl-containing group of 1 to about 12 carbon atoms and may be saturated or unsaturated aliphatic or cycloaliphatic, aryl, alkaryl, aralkyl, or any of the preceding containing a hetero atom such as oxygen, sulfur, nitrogen or phosphorus, and R''' may be substituted with one or more heteroatom-containing substituents such as halides, with the proviso that in an alcoholysis reaction, R''' is other than R". The products can be represented by the formula R'C(O)OR'''.

The processes of this invention can be used to simultaneously produce more than one equilibrium product. For instance, more than one acid or ester can be used or more than one alcohol can be used to form a mixture of esters. For example, a product stream containing one ester product and a higher boiling ester product may be recovered from the single reaction zone, either both in a vapor stream or one in the vapor stream and the other in a liquid product stream. As an illustration involving the simultaneous production of butyl acrylate and ethylhexyl acrylate, butyl acrylate may be recovered from the single reaction zone in. a vapor stream and ethylhexyl acrylate may be recovered in a liquid stream.

Particularly attractive uses of the processes of this invention are in the production of acetates, acrylates, propionates and methacrylates wherein R''' is 1 to about 12 carbons, preferably 1 to 11, more preferably 3 to 8, and most preferably 3 to 6, carbon atoms. Examples of alcohols include methanol, ethanol, iso-propanol, n-butanol, isobutanol, pentanol, hexanol, 2-ethyl hexanol, methoxypropanol, ethoxyethanol, methoxyethanol, methoxybutanol, ethoxypropanol, ethoxybutanol, butoxyethanol, butoxyethoxyethanol, ethoxyethoxyethanol, and methoxyethoxyethanol. The carboxylic acid feed preferably contains 2 to 4 carbons such as acetic acid, acrylic acid, propionic acid, and methacrylic acid.

The processes of this invention are conducted at temperatures within the range of from about 50° C. to about 200° C., preferably from about 100° C. to about 160° C., and more preferably from about 125° C. or 135° C. to about 150° C. Temperatures too low result in lower reaction rates and temperatures too high result in more byproducts and have higher corrosion rates. The reaction zone temperature (together with pressure) should be sufficient to crack heavies, e.g., Michael-Addition heavies, formed in or introduced into said single reaction zone and to vaporize at least a portion of the ester product upon production thereof. However, the reaction zone temperature should not cause undue degradation of reactants, desired products, any catalyst used or desired side reactions. Where a reactant contains another reactive group, e.g., unsaturation in the case of acrylic and methacrylic moieties, the temperature should be such as to not cause undesirable side reactions. To some extent, the polymerization reactions can be controlled by the use of inhibitors as described herein, and thus the temperature of the reaction will also be influenced by inhibitor concentration.

The pressure under which the equilibrium-limited reactions can be conducted can also vary widely. Typically, pressures range from subatmospheric to superatmospheric, e.g., from about 0.01 to 100 bar, most often from about 0.1 to 10 or 15 bar, absolute. As indicated above, the reaction zone temperature and pressure should be sufficient to crack heavies, e.g., Michael-Addition heavies, formed in or introduced into said single reaction zone and to vaporize at least a portion of the ester product upon production thereof.

The reaction may be conducted in the presence of a solvent or one or more of the reactants, products, co-products and side reaction products may comprise the liquid media for the reaction. Where a solvent is used, it is preferably substantially inert and is substantially non-volatile under reaction conditions.

Many equilibrium-limited reactions employ the use of a catalyst to facilitate the exchange reactions. Catalysts appropriate for the equilibrium-limited reaction can be used in the processes of this invention. For esterification, catalysts are often acids such as sulfuric acid, sulfonic acids and acidic exchange resins, and for alcoholysis reactions, metal oxides and alkoxides such as of alkali, alkaline earth, transition and rare earth metals, lead, bismuth and tin and the like. The amount of catalyst can vary widely. Homogeneous catalysts are often used in the range of about 0.001 to 10 or 20 weight percent of the liquid menstruum, and heterogeneous catalysts typically comprise about 10 to 60 percent of the volume of the reaction zone. Lower catalyst concentrations result in lower esterification and cracking rates and a higher purge from the single reaction zone. Higher catalyst concentrations make more byproducts and have higher corrosion rates. When employing sulfonic acid catalysts such as dodecylbenzene sulfonic acid (DBSA), a small amount of water should be present, e.g., from about 0.5 weight percent or less to about 1 weight percent or greater, preferably less than about 1 weight percent, in the single reaction zone to minimize the formation of the sulfonate ester.

Other adjuvants may be contained in the liquid reaction media such as antioxidants, stabilizers, buffers, polymerization inhibitors and the like. This invention is not intended to be limited in any manner by the permissible adjuvants. Phenothiazine (PZ) is the preferred primary process inhibitor. Since PZ is not soluble in water, hydroquinone (HQ) is preferably used as the inhibitor for aqueous streams. Monomethyl ether of hydroquinone (MEHQ) is the preferred product shipping inhibitor and is used in the ester distillation column. Air or oxygen is used to enhance the effectiveness of the inhibitors. A partial pressure of oxygen of from about 0.05 to about 1.0, preferably from about 0.1 to about 0.8, mm Hg at the column base is preferred for all the columns except the water column.

The single reaction zone may be a stirred or agitated tank. In a preferred embodiment, an overhead vapor stream is taken to remove product/co-product (e.g., ester/water from the esterification of alcohol with carboxylic acid) and thus drive the reaction further toward conversion to the desired product. The overhead vapor stream is then subjected to a separation operation such as distillation to recover crude product for further refining and also to recover reactants, e.g., alcohol, and adjuvants, e.g., polymerization inhibitors, for recycle purposes.

Generally, the residence time of the liquid menstruum in the single reaction zone is sufficient to yield production in a concentration within 50, typically within about 70, and sometimes at least about 90 or 95, percent or greater of the theoretical equilibrium concentration of the product in the reaction menstruum under the conditions of the reaction (for given reactant concentrations). The single reaction zone residence time is not narrowly critical and typically ranges from about one hour or less to about 20 hours or more, preferably from about 2 hours to about 10 hours.

The relative amounts of the reactants fed to the single reaction zone may also vary widely and will often be selected based upon economic factors. In many commercial equilibrium-limited reaction processes, the reactants are fed in an approximately stoichiometric ratio for producing the desired product, plus any additional amounts required to make up for losses due to side reactions. Often, for esterification and alcoholysis reactions, the mole ratio of the fresh alcohol to fresh acid or ester is between about 0.9:1 to about 1.1:1 or higher. Preferably, the single reaction zone is operated such that an amount equivalent to at least about 50, preferably at least about 70, and most preferably between about 75 and 90, percent of the fresh feed of at least one of the reactants is consumed.

It should be understood that the amount of the reactants, and their relative concentrations, in the single reaction zone may be different than that of the fresh feed due to recycling of unreacted reactants. Generally, any recycle of reactants is to the single reaction zone or acid separation column in order to enhance the driving force to the sought product. About 0 to 100, preferably about 40 to 60, percent of alcohol recycle is fed to the single reaction zone and the remainder fed to the acid separation column base to stabilize operation thereof. Excess alcohol, e.g., butanol, is preferably fed to the single reaction zone to drive carboxylic acid, e.g., acrylic acid, conversion toward completion. It is desired to keep the mole ratio of the alcohol to acid or ester below about 2:1 in the single reaction zone because a lower ratio makes less byproducts, e.g., butyl ether, which results in lower capital and operating costs. If the mole ratio of the alcohol to carboxylic acid or ester in the reactor feeds is too low, the acid conversion will be low resulting in carboxylic acid buildup in the single reaction zone, carboxylic acid breakthrough in the acid separation column make, high viscosity of the reactor material and/or high reactor purge.

The conditions of the single reaction zone are maintained such that the product is, preferably, produced in the liquid phase and then vaporized. The reaction zone conditions are sufficient to crack heavies, e.g., Michael-Addition heavies, formed in or introduced into said single reaction zone, and to vaporize at least a portion of the ester product upon production thereof. Preferably, an azeotroping agent is present to lower the boiling point of the product to avoid deleterious effects of high temperatures or expensive, high vacuum. Examples of azeotropic esterifications are set forth in Table 1.

TABLE 1

Water-Esters Azeotropes

| Acids | nbp, °C. | Alcohol | nbp, °C. | Esters | nbp, °C. | Water-Ester Azeotropes nbp, °C. | Water weight percent |
|---|---|---|---|---|---|---|---|
| Acetic Acid | 118.5 | Ethanol | 78.3 | EAC | 77.2 | 70.4 | 8.5 |
|  |  | n-propanol | 97.2 | n-PAC | 101.6 | 82.4 | 14 |
|  |  | i-propanol | 82.5 | i-PAC | 88.6 | 76.6 | 10.6 |
|  |  | n-butanol | 117.8 | n-BAC | 126.2 | 90.2 | 28.7 |
|  |  | i-butanol | 108.0 | i-BAC | 117.2 | 87.4 | 16.5 |
|  |  | 2-ethylhexanol | 184.6 | EHAC | 198.4 | 99.0 | 73.5 |
| Acrylic Acid | 140.5 | Ethanol | 78.3 | EA | 99.5 | 81.1 | 15.0 |
|  |  | n-propanol | 97.2 | n-PA | — | — | — |
|  |  | i-propanol | 82.5 | i-PA | — | — | — |
|  |  | n-butanol | 117.8 | n-BA | 147 | 94.5 | 40 |
|  |  | i-butanol | 108.0 | i-BA | — | — | — |
|  |  | 2-ethylhexanol | 184.6 | EHA | — | — | — |
| Propionic Acid | 140.9 | Ethanol | 78.3 | EP | 99.2 | 81.2 | 10 |
|  |  | n-propanol | 97.2 | n-P | 122.1 | 88.9 | 23 |
|  |  | i-propanol | 82.5 | i-P | 110.3 | 85.2 | 19.9 |
|  |  | n-butanol | 117.8 | n-P | 146.8 | 94.8 | 41 |
|  |  | i-butanol | 108.0 | i-P | 136.9 | 92.8 | 52.2 |
|  |  | 2-ethylhexanol | 184.6 | EHP | — | — | — |
| Methacrylic Acid | 160.5 | Ethanol | 78.3 | EMA | — | — | — |
|  |  | n-propanol | 97.2 | n-MA | — | — | — |
|  |  | i-propanol | 82.5 | i-MA | — | — | — |
|  |  | n-butanol | 117.8 | n-MA | — | — | — |
|  |  | i-butanol | 108.0 | i-MA | — | — | — |
|  |  | 2-ethylhexanol | 184.6 | EHMA | — | — | — |

AC = Acetate
A = Acrylate
AC = Acetate
A = Acrylate
E = Ethyl
P = Propyl
B = Butyl
EH = 2-ethylhexyl
P = propionate
MA = Methacrylate Preferably, under the conditions of the single reaction zone including any azeotrope formation, the vapor-liquid equilibrium for the at least one product is such that less than about 50, preferably less than about 30, percent of the product in the single reaction zone is in the liquid phase. The liquid menstruum in the single reaction zone should be mixed well to ensure uniform concentrations and temperature. It may be desirable to employ a forced or natural circulation calandria to supply heat and mixing to the single reaction zone.

Often the reactions in the single reaction zone are conducted at temperatures within the range of about 100° C. to 160° C., more typically about 125° C. or 135° C. to about 150° C., but below a temperature that causes undue degradation of the reactants, desired products, catalyst or desirable side reactions. The reaction zone temperature (together with pressure) should be sufficient to crack heavies, e.g., Michael-Addition heavies, formed in or introduced into said single reaction zone and to vaporize at least a portion of the ester product upon production thereof. Where a reactant contains another reactive group, e.g., unsaturation in the case of acrylic and methacrylic moieties, the temperature should also be below that which causes undesirable side reactions such as polymerization. Polymerization inhibitors may be used to extend the desirable temperature range for the reaction. The pressure in the single reaction zone can also vary widely. Typically, pressures range from subatmospheric to superatmospheric, e.g., from about 0.01 to 100 bar, most often from about 0.1 to 10 or 15 bar, absolute.

The reaction in the single reaction zone is conducted in the presence of liquid comprising at least one of (A) at least one of said reactants, (B) a product other than the substantially vaporized product, where more than one product is intended to be formed, (C) a co-product other than a substantially vaporized co-product, and (D) at least one other liquid component, e.g., a solvent.

Vapor is withdrawn from the single reactor and comprises (i) at least one of the reactants, (ii) the product, and (iii) the co-product.

Where the equilibrium-limited reaction is an esterification or alcoholysis reaction, it is possible for the acid or ester to dimerize or generate other heavies. For the esterification of acrylic acid and butanol to form butyl acrylate, the heavies are formed by a Michael-Addition reaction and as depicted by the following equation:

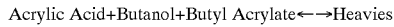

Acrylic Acid+Butanol+Butyl Acrylate←→Heavies

The dimer or heavies product is typically an equilibrium product. The processes of this invention facilitate cracking of the dimer and other heavies. Particularly, the single reaction zone can be operated at sufficiently high temperatures to crack the dimer and heavies, and the dimer and heavies may comprise a substantial portion of the liquid menstruum, for instance, at least about 10 or, more typically, about 20 to 90 or more, weight percent of the menstruum. The heavy residues, including uncrackable heavies and polymers, are purged via the single reaction zone tails.

In contrast to prior art processes in which the acid separation column is mounted onto the reactor and functions as a rectification column (see, for example, European Patent No. 0 733 617), the acid separation column in this invention is positioned apart from the single reaction zone and functions as an acid separation column with both a rectification zone and stripping zone. The rectification zone is above the point where the withdrawn vapor from the single reaction zone is introduced into the acid separation column and the stripping zone is below the point where the withdrawn vapor from the single reaction zone is introduced into the acid separation column. Such a configuration offers many advantages. At least a portion of the withdrawn bottoms fraction from the acid separation column can be supplied to the single reaction zone by controlled means sufficient to provide stable and efficient operation of both the acid separation column and single reaction zone. The rate of supply of withdrawn bottoms fraction from the acid separation column to the single reaction zone can be controlled and adjusted according to the needed water rate for formation of the product/water azeotrope, e.g., butyl acrylate/water azeotrope, as indicated above. As indicated above, by this configuration, the upper portion of the acid separation column can function as a rectification zone (providing enhanced separation of product/reactant, e.g., butyl acrylate/acrylic acid) and the lower portion can function as a stripping zone (reducing product, e.g., butyl acrylate, recycle to the single reaction zone).

The processes of this invention will be further described with respect to the esterification of acrylic acid with butanol. While this is a preferred manner to produce butyl acrylate, it is not intended to limit the broader aspects of this invention.

As a brief overview, butyl acrylate is prepared by acid catalyzed esterification of acrylic acid with butanol. In the process, acrylic acid is esterified with a homogeneous acidic catalyst in a single reaction zone. Butyl acrylate and by-products, substantially free of acrylic acid, are recovered in the acid separation column overhead make. Butyl acrylate is removed essentially via a butyl acrylate/water azeotrope. This overhead make is refined to give essentially pure butyl acrylate. A tails stream from the acid separation column containing water, unreacted feeds, and by-product is sent back to the reactor in order to increase conversion.

With reference to the FIGURE, butanol and acrylic acid (including any recycle) are fed to reactor 100 in a mole ratio of butanol:acrylic acid between about 1:1 to about 2:1. The acrylic acid and butanol supplied to the reactor 100 are typically of standard purities. However, as a result of the processes of this invention, higher concentrations of typical impurities in the acrylic acid stream are better tolerated. For example, the acrylic acid feed to reactor 100 may contain up to 0.2 or more weight percent acetic acid because the acetic acid can react with butanol to form butyl acetate, a light component that can be readily removed by employing this invention. Other impurities, such as acrylic acid dimer, commonly present in the acrylic acid feed, are also tolerated: dimer, for example, is readily cracked by the high temperature operation of the reactor 100 as discussed herein. Similarly, as a result of the unique refining scheme, it is possible to easily remove dibutyl ether, the main impurity in butanol, which allows the use of a lower grade butanol feed. The ability to use a wide range of acid and alcohol leads to significant economic savings.

The reaction is carried out in the presence of an acidic catalyst. Illustrative acidic catalysts include, for example, sulfuric acid, phosphoric acid, and resins that contain acid functional groups. Preferably, the catalyst is a long chain alkyl benzene sulfonic acid such as dodecylbenzene sulfonic acid (DBSA). DBSA catalyst and variations of it are described in U.S. Pat. No. 5,231,222, the disclosure of which is incorporated herein by reference. Relative to other catalysts, DBSA generates significantly less dibutyl ether and heavies during the esterification of acrylic acid with butanol; hence, higher efficiencies are achieved with DBSA as a result of low dibutyl ether and heavies formation. However, DBSA is a homogeneous catalyst; thus, it is subject to entrainment. Nonetheless, the reaction is carried out using DBSA because in the present processes any entrained DBSA is simply cycled via line 15 between reactor 100 and acid separation column 210. The reactor 100 and acid separation column 210 and supply lines 14 and 15 are constructed of materials resistant to corrosion by the acid catalyst.

The catalyst concentration can vary over a wide range. In reactor 100, the DBSA can vary from about 1 to 25, preferably about 3 to 20, and more preferably about 5 to 15, weight percent of the liquid menstruum. DBSA is purged, thus, catalyst make-up to reactor 100 can be a solution of the catalyst with acrylic acid, butanol, recycle liquid or any other process stream.

It is well known in the art that chemical inhibitors can be employed to inhibit the formation of polymers derived from acrylic acid and/or butyl acrylate. Inhibitors are provided to acid separation column 210 via line 16. The inhibitors include phenothiazine (PZ), hydroquinone (HQ), and monomethyl ether of hydroquinone (MEHQ). It is generally accepted that polymer formation occurs in areas where the temperature is high, such as the reactor and distillation columns, or in those areas where vapor condenses on cold surfaces. PZ is utilized in organic streams and HQ and/or MEHQ in water streams. The amount of inhibitors used depends on the process. The chemical inhibitors in reactor 100 will be about 50 to 30,000, e.g., about 10,000, ppm by weight based upon the weight of the liquid menstruum.

Besides the chemical inhibitors, oxygen is added to reactor 100 to enhance the inhibition of polymer formation. Use of oxygen is well known in the art. The oxygen can be added as pure oxygen, as a mixture with an inert gas, or preferably as air. The oxygen is supplied by an air sparger provided at the bottom of the reactor (not shown).

Reactor 100 is a tank type reactor for the reaction of acrylic acid with butanol and removal of butyl acrylate/water azeotrope in order to force the equilibrium to acrylate. Acrylic acid conversion of about 90 percent or higher is desired. A portion of the liquid in reactor 100 may be taken to a calandria (not shown) for increasing the temperature of the liquid. The volume turnover rate through a calandria must assure that the contents of the reactor are well agitated and more uniformly heated. Alternatively, a jacketed reactor designed to generate the requisite heat and provided with mechanical stirrers could be used in place of the tank reactor and calandria.

The temperature in reactor 100 can range from 100° C. to 160° C. but it is most preferred to maintain the temperature within the range of 125° C. or 135° C. to about 150° C. The temperature should be sufficient so as to not only facilitate the conversion of the butanol and acrylic acid to product, but very importantly, under these conditions, enable the heavies to be cracked back to butyl acrylate, acrylic acid and butanol. The average residence time in reactor 100 is about 4 to 10 hours. The pressure in reactor 100 is maintained at about 200 to 600 mm Hg absolute (about 0.3 to 0.8 bar absolute). The liquid in reactor 100 contains about 1 weight percent water and is in a single phase. The heavy residues, including catalyst, inhibitor, uncrackable heavies and polymers, are purged from reactor 100 via line 13.

The reactor purge via line 13, which can contain substantial amounts of acrylic acid and butyl acrylate, may be sent to a separator, e.g., a wiped film evaporator, to recover useful materials. The recovered material may then be recycled to reactor 100 or other suitable point in the process.

The esterification reaction generates water which is removed from reactor 100 and supplied to the lower portion of acid separation column 210 as an azeotrope, e.g., butanol/butyl acrylate/water azeotrope. As stated before, removing water drives the reaction toward butyl acrylate. Acid separation column 210 is of standard engineering design and can use trays or packing. To accommodate any entrainment of the DBSA catalyst, the bottom trays may need to be constructed of a metal which can handle highly corrosive liquid. To prevent polymerization and other fouling reactions in the acid separation column 210, conventional inhibitors such as hydroquinone and phenothiazine are introduced throughout acid separation column 210, diluted by butanol or some other process liquid.

As indicated above, butyl acrylate, water and lights are removed as a vapor from reactor 100 and supplied via line 14 to an intermediate point of acid separation column 210. The primary purpose of acid separation column 210 is to recover butyl acrylate, essentially free of acrylic acid, from the vapor stream of reactor 100. A secondary purpose is to recycle a water-containing stream either directly back to reactor 100 or indirectly back to reactor 100 through a calandria. The acid separation column 210 functions as an acid separation column with both a rectification zone and a stripping zone as described herein.

The separation in the acid separation column 210 is between the lower boiling water/butyl acrylate azeotrope and acrylic acid. The overhead vapor from the acid separation column 210 is condensed and decanted. Part of the water layer is used as a reflux and part of the organic layer is also used for reflux to enhance separation. The organic reflux may be replaced by any butyl acrylate-containing stream from the process. Preferably, balanced water and organic profiles are maintained in the acid separation column 210 to achieve stable and optimal operation thereof. Balanced profiles can be maintained by using a reflux ratio control on the organic make and a column temperature control on the water make. Generally, a 10 to 90 weight percent proportion of the organic layer and a 50 to 100 weight percent proportion of the aqueous layer is recycled to the upper portion of the acid separation column to obtain balanced water and organic profiles.

In a certain composition range, the material in the lower portion of acid separation column 210 can undergo foaming. Foaming carries liquid from the lower portion to the upper portion of the acid separation column 210 and results in acrylic acid breakthrough in the overhead make. It has been found that operational stability can be imparted to the acid separation column 210 through introduction of an alcohol, either fresh or recycled, into the acid separation column 210 in the region between the bottom of the acid separation column 210 and the point where the withdrawn vapor from the single reaction zone 100 is introduced into the acid separation column 210. Preferably, from about 0.1 weight percent to about 10 weight percent of alcohol is maintained in the lower portion of the acid separation column 210 to provide operational stability.

The acid separation column tails flow rate via line via line 15 should be adjusted according to the needed water rate for the butyl acrylate/water azeotrope, which contains about 60 weight percent butyl acrylate and about 40 weight percent water. If the tails rate is too low, the liquid level in the reactor 100 will rise due to buildup of the butyl acrylate concentration. If the tails rate is too high, the excess water will remove butyl butoxy propionate (BBP) from the reactor 100 by the BBP/water azeotrope, which results in a higher BBP concentration in the acid separation column 210 leading to unstable operation.

The overhead from the acid separation column 210 is removed via line 17 and supplied to a condenser/separator (not shown). In the condenser/separator, the vapor is condensed and the liquid is phase separated, with the organic phase being supplied via line 18 to the splitter distillation column 310 and the aqueous phase being sent via lines 17 and 19 to the water distillation column 610 to remove dissolved organics from the aqueous phase.

Water is fed to reactor 100 via recycle from acid separation column 210 in order to maintain a concentration of about 1 weight percent of the liquid menstruum for effective catalyst operation. The concentration of DBSA in reactor 100 is about 1 to 25, preferably about 5 to 15, e.g., 10, weight percent based upon the weight of the liquid menstruum. Inhibitor is added throughout reactor 100 to reduce polymerization.

The base of acid separation column 210 is heated. The top of acid separation column 210 may be at a pressure of 300 mm Hg absolute (about 0.4 bar absolute). To remove butyl acrylate out of reactor 100 effectively, the acid separation column can be operated under vacuum to lower the boiling point of the water/butyl acrylate azeotrope. The liquid at the bottom of acid separation column 210 contains about 20 to 60 weight percent water and 40 to 80 weight percent organics (mostly acrylic acid). This bottoms fraction is returned via line 15 to reactor 100. This recycle step assists in maintaining a water concentration of about 1 weight percent in reactor 100 and supplying water for the water/butyl acrylate azeotrope.

The feed for splitter distillation column 310 is the organic stream from acid separation column 210, which consists mainly of butyl acrylate along with some butanol, lights, and heavies. The purpose of splitter distillation column 310 is, as described earlier, to separate the stream into a tails fraction containing butyl acrylate and heavies, and an overhead stream of butanol, butyl acrylate, and lights such as dibutyl ether and butyl acetate. The tails fraction is essentially free of all light components. The column design is consistent with conventional engineering practice and can use packing or trays. In this embodiment, the base temperature of the splitter distillation column 310 is about 120° C. with a base pressure of about 400 mm Hg (0.6 bar absolute).

The overhead from the splitter distillation column 310 is supplied to a condenser/separator (not shown). In the condenser/separator, the vapor is condensed and the liquid is phase separated, with a portion of the organic phase being supplied via line 20 to the alcohol distillation column 410 and the aqueous phase being sent via line 19 to the water distillation column 610 to remove dissolved organics from the aqueous phase. A portion of the organic layer is used as a reflux to the splitter distillation column 310.

The alcohol distillation column 410 separates the overhead stream from splitter distillation column 310 into a tails stream consisting essentially of butanol and butyl acrylate and an overhead stream consisting essentially of lights, mainly dibutyl ether and butyl acetate. The lights stream is supplied to a condenser/separator (not shown). In the condenser/separator, the vapor is condensed and the liquid is phase separated, with a portion of the organic phase being purged and a portion of the aqueous phase being sent to the water distillation column 610 to remove dissolved organics from the aqueous phase. The remaining portion of the organic phase and aqueous phase are used as reflux to build an azeotrope profile in the alcohol distillation column 410. A high reflux ratio may be used to minimize efficiency loss. As indicated above, a portion of the lights stream is sent via line 21 to waste treatment or may be sold or burned and the tails stream is recycled via line 22 back to either or both of reactor 100 and acid separation column 210. The design of alcohol distillation column 410 is consistent with conventional engineering practice and can use packing or trays. The base temperature of alcohol distillation column 410 is about 80° C. with a pressure of about 300 mm Hg (0.4 bar absolute).

The tails fraction from splitter distillation column 310 is supplied via line 23 to ester distillation column 510. Ester distillation column 510 separates the tails fraction into an overhead stream of butyl acrylate and a tails stream of heavies (and butyl acrylate). The tails stream is recycled via line 24 to either or both of reactor 100 and acid separation column 210 and/or is recycled to the other distillation columns. The tails stream also contains inhibitors which, as described earlier, are desirably recycled. The column design is consistent with conventional engineering practice and can use packing or trays. The base temperature of the column is about 100° C. with a pressure of about 100 mm Hg (0.2 bar absolute). Alternatively, a vapor stream can be withdrawn from the bottom portion or base of splitter distillation column 310 and condensed to form a stream of butyl acrylate, thus eliminating the need for ester distillation column 510.

The unique processes of this invention allow for the recycle of heavies and inhibitors. In conventional processes the entire heavies stream containing the inhibitors is typically discarded. Conventional processes which employ a neutralization step to remove acrylic acid, instead of using an acid separation column as provided in this invention, can not reuse the bottoms fraction from the ester distillation column as inhibitor solution because of the buildup of residue sodium or other alkali metals in that stream. Conventional processes whose reaction conditions are not suitable for cracking heavies can not reuse the bottoms fraction from the ester distillation column as inhibitor solution because it would lead to a buildup of heavies in the reactor. Thus the processes of this invention enable lower inhibitor usage and reduced inhibitor cost as well as more efficient recovery of heavies.

A preferred process for refining a butyl acrylate-containing stream containing butyl acrylate, dibutyl ether, butyl acetate, heavies and butanol is disclosed in copending patent application Ser. No. 08/859,143, filed May 20, 1997, the disclosure of which is incorporated herein by reference.

In the processes of this invention, butyl acrylate can be produced having the preferred composition as described in Table 2 below. Acrylates with such low levels of lights, especially dibutyl ether, exhibit significantly reduced odor as compared to commercially available acrylates and enable the production of unexpectedly high quality product from lower quality feedstock.

TABLE 2

| Component | Typical Ranges (wt. %) | Preferred (wt. %) |
| --- | --- | --- |
| Butyl Acrylate | 95.0 to 100 | 99.5 to 100 |
| Butyl Acetate | 0.000 to 0.05 | 0.000 to 0.01 |
| Butanol | 0.000 to 0.01 | 0.000 to 0.01 |
| Acrylic Acid | 0.000 to 5 | 0.000 to 0.01 |
| Dibutyl Ether | 0.000 to 0.1 | 0.000 to 0.02 |
| Heavies | 0.000 to 2 | 0.000 to 0.5 |
| Water | 0.000 to 0.5 | 0.000 to 0.05 |

As stated above, the processes of this invention may be used to make other products from equilibrium-limited reactions. The following example is provided to further illustrate this invention. Reference is made in the example to the FIGURE. All parts and percentages are by weight unless otherwise indicated or clear from the context.

EXAMPLE 1

339 grams/hour of acrylic acid and 348 grams/hour of n-butanol were fed continuously to a reactor (100), along with 83 grams/hour of a stream (22) containing recycle butanol and inhibitor. The reactor (100) contained a 3.5 liter liquid resident in the reactor for a period of 6 to 7 hours at a temperature of 137° C. and pressure of about 550 mm Hg absolute. Dodecylbenzene sulfonic acid (DBSA) diluted in butyl acrylate was added at a rate of 7 grams/hour. A purge stream (13) was removed from the reactor at a rate of 20 grams/hour. A vapor stream was removed from the reactor and was introduced into an acid separation column (210). Additionally, 113 grams/hour of a stream (22) containing recycle butanol and inhibitor was added to the lower portion of the acid separation column. The acid separation column was operated at a head temperature of 83° C. and pressure of 500 mm Hg. A water rich stream containing acrylic acid (15) was removed from the base of the acid separation column, and was recycled to the reactor at a rate of 760 grams/hour. Vapor was removed from the top of acid separation column (210), and was then condensed and decanted. A portion of the organic phase was returned to the acid separation column and the remaining organic stream, 829 grams/hour, was sent to a splitter distillation column to produce, ultimately, essentially pure butyl acrylate.

The 829 grams/hour organic stream (18) was fed to the middle of the splitter distillation column. The splitter distillation column was operated at 310 mm Hg absolute head pressure and 87° C. head temperature. Butanol, butyl acrylate and light impurities were removed overhead, and butyl acrylate with heavy impurities was removed from the base of splitter distillation column. The overhead from the splitter distillation column was condensed and decanted. A portion of the organic phase was returned to the column and the remaining organic phase (stream 20) was sent to an alcohol distillation column (410) at a rate of 191 grams/hour. The total water phase from the decanter was sent to water distillation column (610) at a rate of 6 grams/hour. From the bottom of the splitter distillation column, a stream (23) was removed at a 666 grams/hour rate and was supplied to an ester distillation column (510).

The alcohol distillation column (410) was operated at 270 mm Hg head pressure and a head temperature of 58° C. A vapor stream concentrated in light impurities was removed overhead from the alcohol distillation column and a butanol rich steam was removed from the base of the alcohol distillation column. The vapor stream was condensed and was decanted to yield an organic phase and water. A portion of the organic phase and water were returned to the alcohol distillation column. The remaining water from the decanter was sent to the water distillation column (610) at a rate of 2 grams/hour. The remainder of the organic phase from the decanter was purged from the system at a rate of 3 grams/hour (stream 21). The butanol rich stream (22) from the bottom of the alcohol distillation column was removed at 196 grams/hour and a portion was returned to the single reactor with the remaining amount returned to the base of the acid separation column.

The ester distillation column was operated at 90 mm Hg head pressure and a head temperature of 79° C. Vapor from the top of the ester distillation column was condensed and was refluxed back to the column at a reflux to distillate ratio of 0.2 grams/grams. From the bottom of ester distillation column a stream (24) was removed at 110 grams/hour and was recycled. From the top of ester distillation column, 99.9 weight percent butyl acrylate was removed at 577 grams/hour.

The compositions of key feedstocks, and compositions of reaction and product streams taken from the reactors and distillation columns, are reported in Table 3 below.

TABLE 3

| Component | AA Feed wt % | BuOH Feed wt % | DBSA Feed wt % | Stream 17 wt % | Stream 18 wt % | Stream 20 wt % | Stream 23 wt % | Stream 21 wt % | Stream 22 wt % | Stream 25 wt % | Stream 24 wt % | Stream 13 wt % | Stream 19 wt % | Stream 15 wt % |
|---|---|---|---|---|---|---|---|---|---|---|---|---|---|---|
| Water | 0.04 | 0.10 | | 11.65 | 2.40 | 7.30 | 0.02 | 6.03 | 5.97 | 0.01 | 0.01 | 1.0 | 96.64 | 45.46 |
| Butanol | | 99.85 | | 13.33 | 14.44 | 58.25 | | 31.12 | 57.88 | | | 0.53 | 3.13 | 6.12 |
| Acrylic Acid | 99.91 | | | | | | | | | | | 12.25 | | 42.79 |
| Butyl Acrylate | | | 50 | 74.80 | 82.93 | 33.52 | 99.96 | 21.96 | 35.99 | 99.98 | 99.68 | 9.52 | 0.12 | 2.54 |
| BBP + HVS | | | | 0.03 | 0.02 | 0.17 | 0.02 | 4.98 | 0.07 | 0.01 | 0.31 | 70.44 | 0.09 | 3.09 |
| Butyl Ether | | 0.05 | | 0.09 | 0.10 | 0.35 | | 18.26 | 0.01 | | | | 0.02 | |
| Butyl Acetate | | | | 0.10 | 0.11 | 0.41 | | 17.65 | 0.08 | | | | | |
| Acetic Acid | 0.05 | | | | | | | | | | | | | |
| DBSA | | | 50 | | | | | | | | | 6.26 | | |
| Total | 100.00 | 100.00 | 100.00 | 100.00 | 100.00 | 100.00 | 100.00 | 100.00 | 100.00 | 100.00 | 100.00 | 100.00 | 100.00 | 100.00 |
| Total, g/hr | 339 | 348 | 7 | 919 | 829 | 191 | 666 | 3 | 196 | 577 | 110 | 20 | 98 | 760 |

Although the invention has been illustrated by the preceding example, it is not to be construed as being limited thereby; but rather, the invention encompasses the generic area as hereinbefore disclosed. Various modifications and embodiments can be made without departing from the spirit and scope thereof.

What is claimed is:

1. A process for conducting an equilibrium-limited reaction of at least one carboxylic acid and at least one alcohol to produce at least one ester product comprising:
   a. reacting at least one carboxylic acid-containing feedstock with at least one alcohol-containing feedstock in the presence of an esterification catalyst selected from the group consisting of a sulfuric acid, a sulfonic acid or an acidic exchange resin in a single reaction zone that is a stirred or agitated vessel, wherein the reaction zone contains about 1 weight percent water or less, maintained under reaction conditions sufficient to produce at least one ester product, said reaction conditions comprising a temperature and pressure sufficient to crack heavies formed in or introduced into said single reaction zone and to vaporize at least a portion of said at least one ester product upon production thereof;

b. withdrawing vapor from said single reaction zone, and introducing said withdrawn vapor into the lower portion of an acid separation column, said acid separation column comprising a rectification zone above the point where said withdrawn vapor is introduced into said acid separation column and a stripping zone below the point where said withdrawn vapor is introduced into said acid separation column, to provide in said rectification zone an overhead fraction comprising said at least one ester product and in said stripping zone a bottoms fraction comprising water and said at least one carboxylic acid;

c. withdrawing from the acid separation column the bottoms fraction and supplying at least a portion of the withdrawn bottoms fraction to said single reaction zone; and d. withdrawing from the acid separation column the overhead fraction and recovering said at least one ester product from the overhead fraction;

wherein said ester product is represented by the formula R'C(O)OR''', said carboxylic acid is represented by the formula R'C(O)OH, and said alcohol is represented by the formula R'''OH wherein R' is a hydrocarbyl-containing group of 1 to about 8 carbon atoms and R''' is a hydrocarbyl-containing group of 1 to about 12 carbon atoms.

2. The process of claim 1 wherein said at least one carboxylic acid-containing feedstock comprises a crude acrylic acid stream containing acetic acid, acrylic acid dimer and/or other Michael-Addition heavies, and said at least one alcohol-containing feedstock comprises a crude butanol stream containing butyl ether.

3. The process of claim 1 wherein said at least one carboxylic acid-containing feedstock and/or said at least one alcohol-containing feedstock comprise a heavy residue-containing stream generated from another process which employs an equilibrium-limited reaction.

4. A process for conducting an equilibrium-limited reaction of at least one carboxylic acid and at least one alcohol to produce at least one ester product comprising:

a. reacting at least one carboxylic acid-containing feedstock with at least one alcohol-containing feedstock in the presence of an esterification catalyst selected from the group consisting of a suluic acid, a sulfonic acid or an acidic exchange resin in a single reaction zone that is a stirred or agitated vessel, wherein the reaction zone contains about 1 weight percent water or less, maintained under reaction conditions sufficient to produce at least one ester product, said reaction conditions comprising a temperature and pressure sufficient to crack heavies formed in or introduced into said single reaction zone and to vaporize at least a portion of said at least one ester product upon production thereof;

b. withdrawing vapor from said single reaction zone, and introducing said withdrawn vapor into the lower portion of an acid separation column, said acid separation column comprising a rectification zone above the point where said withdrawn vapor is introduced into said acid separation column and a stripping zone below the point where said withdrawn vapor is introduced into said acid separation column, to provide in said rectification zone an overhead fraction comprising said at least one ester product and in said stripping zone a bottoms fraction comprising water and said at least one carboxylic acid;

c. introducing at least one alcohol, which may be the same or different as the alcohol contained in said alcohol-containing feedstock, into said acid separation column in the region between the bottom of the acid separation column and the point where said withdrawn vapor is introduced into the acid separation column, d. withdrawing from the acid separation column the bottoms fraction and supplying at least a portion of the withdrawn bottoms fraction to said single reaction zone; and e. withdrawing from the acid separation column the overhead fraction and recovering said at least one ester product from the overhead fraction;

wherein said ester product is represented by the formula R'C(O)OR''', said carboxylic acid is represented by the formula R'C(O)OH, and said alcohol is represented by the formula R''OH wherein R' is a hydrocarbyl-containing group of 1 to about 8 carbon atoms and R''' is a hydrocarbyl-containing group of 1 to about 12 carbon atoms.

5. The process of claim 4 wherein the introduced alcohol is fresh or recycled.

6. The process of claim 4 in which carboxylic acid breakthrough in the overhead make from the acid separation column is minimized or eliminated.

7. A process for conducting an equilibrium-limited reaction of at least one unsaturated carboxylic acid and at least one alcohol to produce at least one unsaturated ester product comprising:

a. reacting at least one unsaturated carboxylic acid-containing feedstock with at least one alcohol-containing feedstock in the presence of an esterification catalyst selected from the group consisting of a sulfuric acid, a sulfonic acid or an acidic exchange resin in a single reaction zone that is a stirred or agitated vessel, wherein the reaction zone contains about 1 weight percent water or less, maintained under reaction conditions sufficient to produce at least one unsaturated ester product, said reaction conditions comprising a temperature and pressure sufficient to crack heavies formed in or introduced into said single reaction zone and to vaporize at least a portion of said at least one unsaturated ester product upon production thereof;

b. withdrawing vapor from said single reaction zone, and introducing said withdrawn vapor into the lower portion of an acid separation column, said acid separation column comprising a rectification zone above the point where said withdrawn vapor is introduced into said acid separation column and a stripping zone below the point where said withdrawn vapor is introduced into said acid separation column, to provide in said rectification zone an overhead fraction comprising said at least one unsaturated ester product, lower boiling byproducts, higher boiling byproducts and said at least one alcohol, and in said stripping zone a bottoms fraction comprising water and said at least one unsaturated carboxylic acid, and introducing at least one polymerization inhibitor into said acid separation column;

c. withdrawing from the acid separation column the bottoms fraction and supplying at least a portion of the withdrawn bottoms fraction to said single reaction zone;

d. withdrawing from the acid separation column the overhead fraction and introducing at least a portion of the withdrawn overhead fraction into at least one splitter distillation column to provide an overhead fraction comprising said lower boiling byproducts and said at least one alcohol and a bottoms fraction comprising said at least one unsaturated ester product and said higher boiling byproducts, and introducing at least one polymerization inhibitor into said at least one splitter distillation column;

e. withdrawing from the at least one splitter distillation column the overhead fraction and introducing the withdrawn overhead fraction into at least one alcohol recovery distillation column to provide an overhead fraction comprising said lower boiling byproducts and a bottoms fraction comprising said at least one alcohol, and introducing at least one polymerization inhibitor into said at least one alcohol recovery distillation column;

f. withdrawing from the at least one alcohol recovery distillation column the bottoms fraction and recycling at least a portion of said bottoms fraction and the overhead fraction and purging at least a portion of said overhead fraction;

g. withdrawing from the at least one splitter distillation column the bottoms fraction and introducing the withdrawn bottoms fraction into at least one ester distillation column to provide an overhead fraction comprising said at least one unsaturated ester product and a bottoms fraction comprising said higher boiling byproducts and at least one polymerization inhibitor, and introducing at least one polymerization inhibitor into said at least one ester distillation column and/or said withdrawn bottoms fraction from the at least one splitter distillation column prior to introducing said withdrawn bottoms fraction into said at least one ester distillation column;

h. withdrawing from the at least one ester distillation column the bottoms fraction comprising at least one polymerization inhibitor and supplying at least a portion of the withdrawn bottoms fraction to the acid separation column, the at least one splitter distillation column and/or the at least one alcohol recovery distillation column, in an amount sufficient to minimize or eliminate polymerization of said unsaturated carboxylic acid and/or said unsaturated ester product; and i. withdrawing from the at least one ester distillation column the overhead fraction comprising said at least one unsaturated ester product;

wherein said ester product is represented by the formula R'C(O)OR''', said carboxylic acid is represented by the formula R'C(O)OH, and said alcohol is represented by the formula R'''OH wherein R' is a hydrocarbyl-containing group of 1 to about 8 carbon atoms and R''' is a hydrocarbyl-containing group of 1 to about 12 carbon atoms.

8. The process of claim 7 wherein at least one fresh inhibitor is supplied to the acid separation column, the splitter distillation column, the withdrawn bottoms fraction from the splitter distillation column prior to introducing said withdrawn bottoms fraction into the ester distillation column, and/or the ester distillation column.

9. The process of claim 7 wherein said fresh inhibitor is the same or different.

10. The process of claim 7 wherein at least a portion of the withdrawn bottoms fraction from the alcohol distillation column is recycled and at least a portion of the withdrawn overhead fraction from the alcohol distillation column is purged.

11. A process for conducting an equilibrium-limited reaction of at least one carboxylic acid and at least one alcohol to produce at least one ester product comprising:

a. reacting at least one carboxylic acid-containing feedstock with at least one alcohol-containing feedstock in the presence of an esterification catalyst selected from the group consisting of a sulfuric acid, a sulfonic acid or an acidic exchange resin in a single reaction zone, wherein the reaction zone contains about 1 weight percent water or less, maintained under reaction conditions sufficient to produce at least one ester product, said reaction conditions comprising a temperature and pressure sufficient to crack heavies formed in or introduced into said single reaction zone and to vaporize at least a portion of said at least one ester product upon production thereof;

b. withdrawing vapor from said single reaction zone, and introducing said withdrawn vapor into the lower portion of an acid separation column, said acid separation column comprising a rectification zone above the point where said withdrawn vapor is introduced into said acid separation column and a stripping zone below the point where said withdrawn vapor is introduced into said acid separation column, to provide in said rectification zone an overhead fraction comprising said at least one ester product, lower boiling byproducts, higher boiling byproducts and said at least one alcohol, and in said stripping zone a bottoms fraction comprising water and said at least one carboxylic acid;

c. withdrawing from the acid separation column the bottoms fraction and supplying at least a portion of the withdrawn bottoms fraction to said single reaction zone;

d. withdrawing from the acid separation column the overhead fraction and introducing at least a portion of the withdrawn overhead fraction into at least one splitter distillation column to provide an overhead fraction comprising said lower boiling byproducts and said at least one alcohol and a bottoms fraction comprising said at least one ester product and said higher boiling byproducts;

e. withdrawing from the at least one splitter distillation column the bottoms fraction and introducing the withdrawn bottoms fraction into at least one ester distillation column to provide an overhead fraction comprising said at least one ester product and a bottoms fraction comprising said higher boiling byproducts;

f. withdrawing from the at least one ester distillation column the overhead fraction, comprising at least said one ester product, and the bottoms fraction and recycling at least a portion of said bottoms fraction;

g. withdrawing from the at least one splitter distillation column the overhead fraction and introducing the withdrawn overhead fraction into at least one alcohol recovery distillation column to provide an overhead fraction comprising said lower boiling by products and a bottoms fraction comprising said at least one alcohol;

h. withdrawing from the at least one alcohol recovery distillation column the bottoms fraction and supplying at least a portion of the withdrawn bottoms fraction to said acid separation column in the region between the bottom of the acid separation column and the point where said withdrawn vapor is introduced into the acid separation column; and i. withdrawing from the at least one alcohol recovery distillation column the overhead fraction and purging at least a portion of the withdrawn overhead fraction;

wherein said ester product is represented by the formula R'C(O)OR''', said carboxylic acid is represented by the formula R'C(O)OH, and said alcohol is represented by the formula R'''OH wherein R' is a hydrocarbyl-containing group of 1 to about 8 carbon atoms and R''' is a hydrocarbyl-containing group of 1 to about 12 carbon atoms.

12. The process of claim 11 wherein at least a portion of the withdrawn bottoms fraction from the ester distillation column is recycled and at least a portion of the withdrawn overhead fraction from the alcohol distillation column is purged.

13. The process of claim 11 which further comprises introducing at least a portion of (i) the withdrawn overhead fraction from the acid separation column, (ii) the withdrawn overhead fraction from the at least one splitter distillation column, and/or (iii) the withdrawn overhead fraction from the at least one alcohol recovery distillation column, to a water distillation column to provide an overhead fraction comprising said at least one alcohol and a bottoms fraction comprising water, withdrawing from the water distillation column the bottoms fraction, and withdrawing from the water distillation column the overhead fraction and supplying at least a portion of the overhead fraction to said acid separation column in the region between the bottom of the acid separation column and the point where said withdrawn vapor from the single reaction zone is introduced into the acid separation column and/or said single reaction zone.

14. The process of claim 13 wherein at least a portion of the withdrawn bottoms fraction from the water distillation column is purged.

15. The process of claim 1 wherein the equilibrium-limited reaction is an esterification of a carboxylic acid of 2 to 4 carbons with an alcohol of 1 to about 12 carbons.

16. The process of claim 15 wherein the alcohol comprises n-butanol and the carboxylic acid comprises acrylic acid.

17. The process of claim 1 in which butyl acrylate and ethylhexyl acrylate are simultaneously produced.

18. The process of claim 17 in which both butyl acrylate and ethylhexyl acrylate are recovered from the single reaction zone in a vapor stream or butyl acrylate is recovered from the single reaction zone in a vapor stream and ethylhexyl acrylate is recovered from the single reaction zone in a liquid stream.

19. The process of claim 1 further comprising condensing and decanting said overhead fraction from the acid separation column and recycling a 10 to 90 weight percent proportion of the organic layer and a 50 to 100 weight percent proportion of the aqueous layer to the upper portion of the acid separation column for refluxing.

20. A mixture, generated batchwise or continuously by the process of claim 1, the mixture comprising at least 50.0 weight percent butyl acrylate and containing not more than 8 parts per million acrylic acid.

21. The process of claim 1 in which less than about 1 weight percent water is present in the single reaction zone.

22. A process for conducting an equilibrium-limited reaction of at least one carboxylic acid and at least one alcohol to produce at least one ester product comprising reacting at least one carboxylic acid-containing feedstock with at least one alcohol-containing feedstock in the presence of an esterification catalyst selected from the group consisting of a sulfuric acid, a sulfonic acid or an acidic exchange resin in a single reaction zone, wherein the reaction zone contains about 1 weight percent water or less, maintained under reaction conditions sufficient to produce at least one ester product, said reaction conditions comprising a temperature and pressure sufficient to crack heavies formed in or introduced into said single reaction zone and to vaporize at least a portion of said at least one ester product upon production thereof, and wherein said at least one carboxylic acid-containing feedstock comprises a crude acrylic acid stream containing acetic acid, acrylic acid dimer and/or other Michael-Addition heavies, wherein said ester product is represented by the formula R'C(O)OR''', said carboxylic acid is represented by the formula R'C(O)OH, and said alcohol is represented by the formula R'''OH wherein R' is a hydrocarbyl-containing group of 1 to about 8 carbon atoms and R''' is a hydrocarbyl-containing group of 1 to about 12 carbon atoms.

23. The process of claim 22 wherein said crude acrylic acid stream contains greater than about 0.5 weight percent of acetic acid, acrylic acid dimer and/or other Michael-Addition heavies.

24. The process of claim 1 wherein said single reaction zone contains a purge stream which comprises acrylic acid and butyl acrylate, said purge stream is treated by a separator, and optionally recovered acrylic acid and butyl acrylate are recycled to said single reaction zone or other suitable point in the process.

25. The process of claim 24 wherein said separator comprises a wiped film evaporator.

* * * * *